(12) United States Patent
Bédard et al.

(10) Patent No.: US 9,370,439 B2
(45) Date of Patent: Jun. 21, 2016

(54) LOAD DISTRIBUTION DEVICE FOR HUMAN JOINTS

(76) Inventors: Stéphane Bédard, St-Augustin-De Desmaures (CA); Dany Lachance, St-Etienne de Lauzon (CA); Benoit Gilbert, Lac Beauport (CA); Yves Roy, Beauport (CA)

( * ) Notice: Subject to any disclaimer, the term of this patent is extended or adjusted under 35 U.S.C. 154(b) by 885 days.

(21) Appl. No.: 13/639,742

(22) PCT Filed: Feb. 18, 2011

(86) PCT No.: PCT/CA2011/000192
§ 371 (c)(1),
(2), (4) Date: Oct. 5, 2012

(87) PCT Pub. No.: WO2011/123928
PCT Pub. Date: Oct. 13, 2011

(65) Prior Publication Data
US 2013/0023800 A1  Jan. 24, 2013

Related U.S. Application Data

(60) Provisional application No. 61/282,835, filed on Apr. 7, 2010.

(51) Int. Cl.
*A61F 5/01* (2006.01)

(52) U.S. Cl.
CPC .............. *A61F 5/0123* (2013.01); *A61F 5/0125* (2013.01); *A61F 2005/0155* (2013.01)

(58) Field of Classification Search
CPC .............. A61H 3/00; A61H 2003/001; A61H 2003/007; A61H 2003/0173–2003/018; A61H 2003/0192–2003/0196; A61H 2201/5061–2201/2069; A61H 2201/5084; A63B 23/04; A63B 23/0494; A61F 5/0102; A61F 5/0123–5/0125; A61F 2005/0144; A61F 2005/0155; A61F 2005/0165–2005/0167
See application file for complete search history.

(56) References Cited

U.S. PATENT DOCUMENTS

| | | | |
|---|---|---|---|
| 7,429,253 B2 * | 9/2008 | Shimada | A61F 5/0102 602/16 |
| 7,578,799 B2 * | 8/2009 | Thorsteinsson | A61B 5/1038 602/16 |
| 8,057,410 B2 | 11/2011 | Angold et al. | |

(Continued)

FOREIGN PATENT DOCUMENTS

EP         1792597 A1 *  6/2007  ............ A61F 5/0102

*Primary Examiner* — Rachel Young
(74) *Attorney, Agent, or Firm* — Equinox IP; Christian Robillard

(57) ABSTRACT

A load distribution device that transfers the musculo-skeletal stress at a joint to associated body segments of a given joint-segments body structure. The device includes a proximal support element adapted to be positioned onto a proximal body segment, a distal support element adapted to be positioned onto a distal body segment, a compensating joint movably connecting the proximal and distal support elements, a control system operatively connected to the compensating joint and a power source supplying power to the control system and the compensating joint. During user executed movements, the compensating joint generates or dissipates, under the directions of the control system a preset level of biomechanical energy corresponding to a user desired musculo-skeletal stress reduction at the joint-segments structure in order to compensate the movements of the user, the biomechanical energy being redistributed onto the proximal and distal body segments via the corresponding proximal and distal support elements.

15 Claims, 7 Drawing Sheets

(56) References Cited

U.S. PATENT DOCUMENTS

| | | | | |
|---|---|---|---|---|
| 2008/0097269 A1* | 4/2008 | Weinberg | A61F 2/68 | 602/16 |
| 2009/0299480 A1* | 12/2009 | Gilbert | A61F 2/582 | 623/18.11 |
| 2010/0160844 A1* | 6/2010 | Gilbert | A61F 2/64 | 602/16 |
| 2010/0268351 A1* | 10/2010 | van der Merwe | A61F 2/68 | 623/24 |

* cited by examiner

LOAD DISTRIBUTION DEVICE FOR HUMAN JOINTS

CROSS-REFERENCE TO RELATED APPLICATIONS

This application claims the benefits of U.S. provisional patent application No. 61/282,835 filed on Apr. 7, 2010, which is herein incorporated by reference.

TECHNICAL FIELD

The present invention relates to a load distribution device for human joints.

BACKGROUND

For the last 10 years, many people have crafted inventions aiming at the assistance of the human mobility in the field of rehabilitation or for specific heavy-duty tasks. Some of them have been designed for the lower extremities, addressing the enhancement or the restoration of the locomotion. Others have been crafted for the upper extremities aiming at the arms' mobility restoration or providing assistance during specific or repetitive tasks. Usually named "Exoskeleton" or "Ectoskeleton", these types of devices perform their task independently of the body structure, they work "outside" the body without interacting intrinsically with the human body while having a mechanical link in order to "move" in sync with the body structure. Current exoskeletons are not designed for a complete merge with the anatomical structures of the human body for a full biomechanical assistance (kinetics and kinematics) nor are they designed for protecting the body structure against acute and chronic biomechanical traumas during high-demanding activities.

For some exoskeletons, we refer to mechanisms named "Load Ground Transfer Exoskeleton for Lower Extremities", in which the main function relates to the transfer of a portion of the body load carried by the user (weight and additional accessories) directly to the ground with an articulated mechanism running in parallel with the body structure. These types of devices are mainly dedicated to supporting a confined additional load and to assist the human body in heavy-duty tasks such as carrying a heavy back pack onto the user's shoulder-back body structure. These devices supply the biomechanical energy at their respective joint mechanisms for the support of the body load and then the mechanical transfer the load to the ground.

Current load ground transfer exoskeletons for lower extremities are equipped with a critical element, a pair of foot-plate, used as a mechanical component located at the end of a serial mechanism ensuring the mechanical transfer of the body load to the ground and a ground reaction force sensor for the control of the apparatus. Moreover, all designs found into the here above devices limit the load ground transfer through one biomechanical plan, which is the lateral plan, commonly called the sagital plan.

The use of foot-plates for the load transfer and the control brings up many functional issues. On irregular grounds, the biomechanical stability of the user and the ground reaction force signals are compromised. Also, the user comfort during locomotion is significantly reduced and the complex mobility of the ankle-foot structure is jeopardized during mid- and long-term use. The "one-plan" mechanical architecture offered by these designs diminishes the capacity of the device to properly assist the user in real-life situations. Even though these designs are efficient for load ground transfer into the main biomechanical plan during locomotion, they still do not provide any assistance or support for the transversal rotations (transversal plan) and for balancing movements (frontal plan) of the body, which means that the user, even wearing this type of devices, would work very hard against the load and its inertia during those movements (rotations and balance), which represents a significant part of the locomotion.

The load ground transfer exoskeleton for lower extremities is an adequate solution for carrying extra load in simple environments but becomes irrelevant in the case where the purpose of the supporting device is to augment the biomechanical capacity and to protect the body structure of the human body for the whole locomotion including any complex movements related to highly demanding activities.

Another category of exoskeletons are the devices named "Assistive Orthopedic Devices for Lower and Upper Extremities". These devices are adequate for rehabilitation while they actively assist the basic mobility of the respective limb. However, current designs do not address the full biomechanical requirements of limbs' mobility. In fact, these designs are not conceived to compensate (in generation and in dissipation) the full kinematics and more specifically the kinetics required to exert efficiently the whole mobility of the said limbs. Moreover, the above-referenced devices do not have the required technical characteristics to allow them to distribute with efficacy the additional biomechanical energy deployed by their respective joint mechanism onto the body structure they are designed to support; resulting into a significant reduction of the mechanical assistance.

A final category of exoskeletons is referred to as "Load Transfer Exoskeletons for the Upper Body". The main function of these devices is to actively assist the overall mobility of the upper extremities by supplying a certain amount of biomechanical energy at their joint mechanisms and transfer the additional effort to a support element located at the trunk of the human body.

These devices are adequate for upper extremities mobility tasks requiring limited torque. In fact, the capacity of the devices to supply kinetic effort at respective joint mechanism is directly related to the stability level of the support element at the trunk. Thus, the capacity of the proposed designs to fulfill the whole biomechanical requirements of the upper extremities mobility is significantly reduced by the fact that the whole part of the additional energy supplied by the device is entirely transferred to the trunk support element rather than being distributed all around the respective limb which could result to the augmentation of the biomechanical capacity as well as the protection the body structure of the respective limb.

Accordingly, there is a need for a device that maintains, restores and/or enhances the mobility of the human body while not being restrictive in terms of maintenance, restoration and enhancement of biomechanical capacity, and consequently exerts a natural body mobility

SUMMARY

The present invention relates to a load distribution device, which can be used individually or as part of a set of two or more devices, worn on one, a pair of or a plurality of joint-segments body structures of the human body, the one or more load distribution devices independently perform their joint-to-segments musculo-skeletal stress transfer function on their respective joint-segments body structure in sync with the human body, the load distribution device comprising:

a load distribution assembly in biomechanical connection with corresponding body segments of the joint-segments structure, the load distribution assembly having a proximal and a distal support elements in biomechanical connection with the proximal and the distal body segments, respectively, of the joint-segments structure, the proximal and the distal support elements supporting at least one pair of contact elements positioned in an antogist-antagonist configuration for the distribution of biomechanical energy onto the respective body segments;

a compensating joint operatively connected between the proximal and the distal support elements, the compensating joint being so configured as to generate and dissipate biomechanical energy;

a control system operatively connected to the compensating joint for controlling the compensating joint's motions in synchronization with the static and the dynamic mobility of the joint-segments structure; and a power source operatively connected to the compensating joint and the control system, the power source providing the required electrical energy for the operation of the load distribution device;

wherein during user executed movements, the compensating joint generates or dissipates, under the directions of the control system a preset level of biomechanical energy corresponding to a user desired musculo-skeletal stress reduction at the joint-segments structure in order to compensate his movements, the biomechanical energy being redistributed onto the body segments of the joint-segments structure via the load distribution assembly for the release of the musculo-skeletal stress at the joint of the joint-segments structure.

More specifically, the present invention relates to a load distribution device that transfers the musculo-skeletal stress at a joint to associated body segments of a given joint-segments body structure of a user, comprising:

a proximal support element adapted to be positioned onto a proximal body segment of the joint-segments body structure, the proximal support element including at least one pair of contact elements positioned in an antogist-antagonist configuration;

a distal support element adapted to be positioned onto a distal body segment of the joint-segments body structure, the distal support element including at least one pair of contact elements positioned in an antogist-antagonist configuration;

a compensating joint movably connecting the proximal and distal support elements;

a control system operatively connected to the compensating joint; and a power source supplying power to the control system and the compensating joint;

wherein during user executed movements, the compensating joint generates or dissipates, under the directions of the control system a preset level of biomechanical energy corresponding to a user desired musculo-skeletal stress reduction at the joint-segments structure in order to compensate the movements of the user, the biomechanical energy being redistributed onto the proximal and distal body segments via the contact elements of the corresponding proximal and distal support elements.

The present invention also relates to a load distribution device as described above wherein the at least one pair of contact elements of the proximal support element include a proximal body segment proximal posterior contact element and a proximal body segment distal anterior contact element, and/or a proximal body segment proximal anterior contact element and a proximal body segment distal posterior contact element, and the at least one pair of contact elements of the distal support element include a distal body segment proximal anterior contact element and a distal body segment distal posterior contact element, and/or a distal body segment proximal posterior contact element and a distal body segment distal anterior contact element.

BRIEF DESCRIPTION OF THE FIGURES

Embodiments of the invention will be described by way of example only with reference to the accompanying drawings, in which.

DEFINITIONS

The detailed description and figures refer to the following terms which are herein defined:

Distal: situated away from the center of the body (i.e. the heart); and

Proximal: situated towards the center of the body (i.e. the heart).

DETAILED DESCRIPTION

Generally stated, the non-limitative illustrative embodiment of the present invention provides a load distribution device that transfers the musculo-skeletal stress at the joint to the body segments of a given joint-segments body structure of a user. More specifically, the present invention relates to a load distribution device, which can be used individually or as part of a set of two or more devices, worn on one, a pair of or a plurality of joint-segments body structures of the human body. The one or more load distribution devices independently perform their joint-to-segments musculo-skeletal stress transfer function on their respective joint-segments body structure as well as in sync with the human body in the case where more than one load distribution device are used.

Example of joint-segments body structures are:

knee joint with the thigh (proximal segment) and shank (distal segment);

elbow joint with the arm (proximal segment) and forearm (distal segment);

ankle joint with the shank (proximal segment) and foot (distal segment); and wrist joint with the forearm (proximal segment) and hand (distal segment).

Although the load distribution device may be used individually or as part of a set of two or more devices, the present invention will be described using an illustrative embodiment in the form of a single device in order to lighten the text.

The load distribution device according the illustrative embodiment of the present invention augments the biomechanical capability of a user while performing tasks that necessitate additional biomechanical energy to maintain, to restore or to enhance the biomechanical capacity of a user with mobility dysfunctions or performing specific or repetitive tasks requiring additional biomechanical energy, and to protect the human body joint structure against acute and chronic injuries.

The design of the load distribution device is an automated dermoskeleton device, i.e. an external orthotic-type supportive device, fully integrated onto a given joint-segments structure of a user's body without any interaction with the environment such as ground contacts using, for example, instrumented insoles. The load distribution device is designed so as to operate exclusively in cooperation with the associated body segments and is governed solely by the movements and the intentions of the user. Therefore, the additional biomechanical energy compensation performed by the load distribution device becomes totally independent of any interaction with the external environment.

Figure 1:
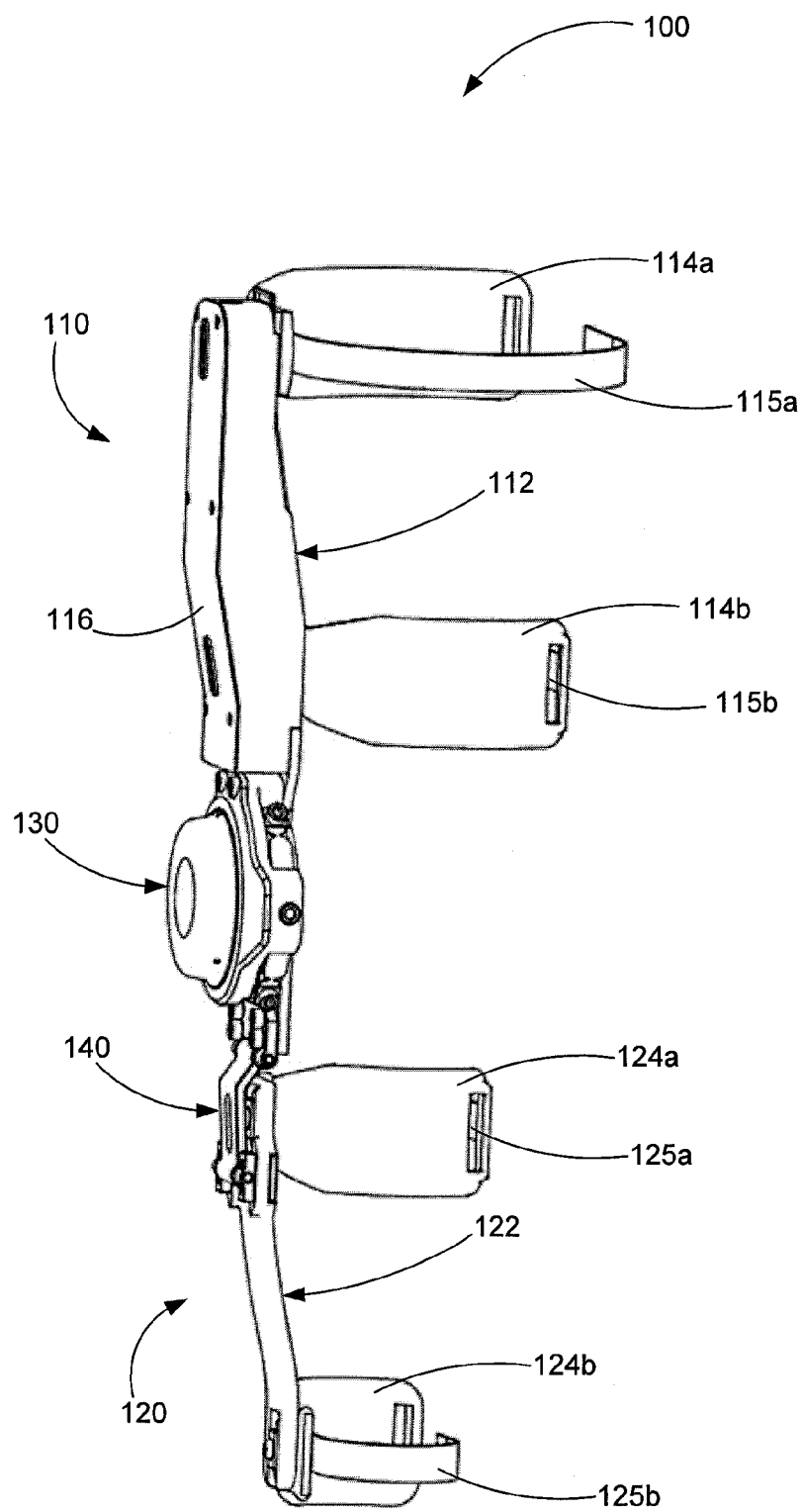
FIG. 1 is a perspective front view of the load distribution device in accordance with an illustrative embodiment of the present invention.
Figure 2:
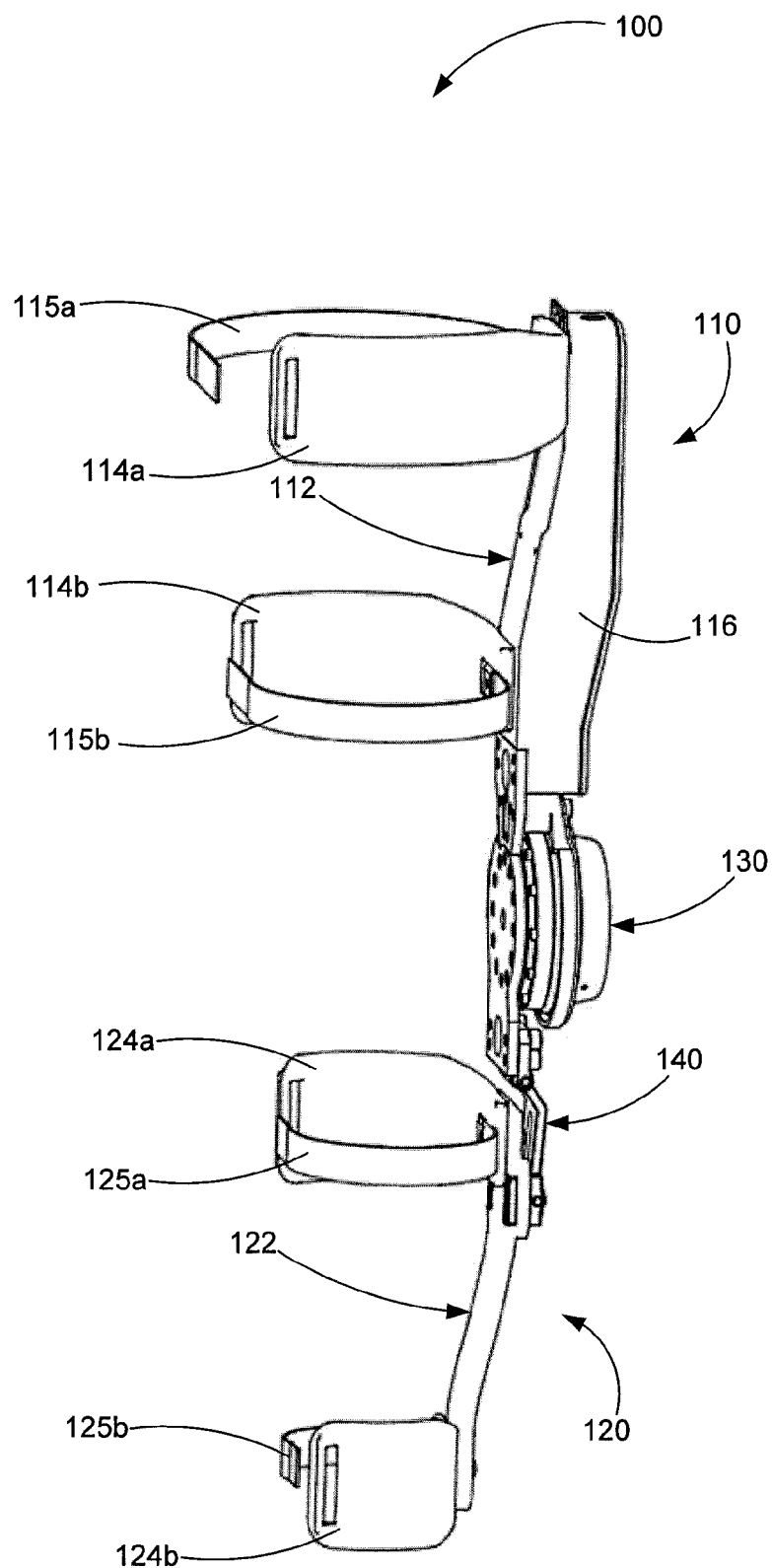
FIG. 2 is a perspective rear view of the load distribution device of FIG. 1.

Referring to FIGS. 1 and 2, the load distribution device 100 is composed of three main components for the compensation and the distribution of the musculo-skeletal stress at joint-segments structure of the human body: a load distributor assembly composed of a proximal 110 and distal 120 support elements, and a compensating joint 130. The load distribution device 100 further includes an enclosure 116 positioned on the proximal support element 110, enclosing electronic components such as a control system (not shown), and a power source, for example a battery pack (not shown). It is to be understood that in an alternative embodiment the electronic components may be positioned elsewhere.

The proximal 110 and distal 120 support elements include respective proximal 112 and distal 122 frame elements supporting associated contact elements 114a, 114b, 115a, 115b, and 124a, 124b, 125a, 125b.

The proximal 112 and distal 122 frame elements have two main purposes: the transfer of loads from the compensating joint 130 to their associated contact elements 114a, 114b, 115a, 115b, and 124a, 124b, 125a, 125b and to provide room for the electronics. The proximal frame element 112 transfers the additional biomechanical energy from the compensating joint 130 to contact elements 114a, 114b and 115a, 115b while the distal frame element 122 transfers the additional biomechanical energy from the compensating joint 130 to contact elements 124a, 124b and 125a, 125b via the multi-degrees-of-freedom (DOF) mechanism 140.

Contact elements 114a, 114b and 124a, 124b, namely proximal segment proximal posterior contact element 114a, proximal segment distal anterior contact element 114b, distal segment proximal anterior contact element 124a and distal segment distal posterior contact element 124b, provide contact with a user's limb and allow the transfer of the musculo-skeletal stress from the load distribution device 100 to the limb's proximal and distal segments during extension. As for contact elements 115a, 115b and 125a, 125b, namely proximal segment proximal anterior contact element 115a, proximal segment distal posterior contact element 115b, distal segment proximal posterior contact element 125a and distal segment distal anterior contact element 125b, they provide contact with a user's limb and allow the transfer of the musculo-skeletal stress from the load distribution device 100 to the limb's proximal and distal segments during flexion.

In the illustrative embodiment illustrated in FIGS. 1 and 2, contact elements 114a, 114b and 124a, 124b are made of a rigid material and have a rounded shape in order to provide a high level of comfort to the user as well as improve the efficiency of the load transfer. In order to provide a better fit to different user morphologies, each contact element 114a, 114b and 124a, 124b is fully adjustable in the sagital plane with three-degrees of freedom (two translations and one rotation). The vertical translation allows adjustment for different user heights, while the antero-posterior translation allows fitting to the user's limb diameter. The rotation in the sagital plane provides final adjustment of the contact surface to the contour of the user's limb to improve comfort. Rigid materials that can be used for the contact elements include composite materials such as carbon fiber and urethane or carbon fiber and ultrahigh molecular weight polyethylene (UHMW-PE) and aluminum. Contact elements made or rigid material can further comprise a contact interface for the user's comfort, for example a neoprene fabric contact interface (in rubber form).

As for contact elements 115a, 115b and 125a, 125b, they are made of a pliant material since the load transfer is at a different level. In order to provide a better fit to different user morphologies, each contact element 115a, 115b and 125a, 125b is also fully adjustable to improve comfort. Pliant materials that can be used for the contact elements include polypropylene fabric, for example in 1.5" (3.8 cm) or 2" (5 cm) wide strips.

It is to be understood that in alternative embodiments, the various contact elements 114a, 114b, 115a, 115b, and 124a, 124b, 125a, 125b may be made of either rigid or pliant material in various combinations. In further alternative embodiments, the load distribution device 100 may be provided either only with contact elements 114a, 114b and 124a, 124b aimed at extension or contact elements 115a, 115b and 125a, 125b aimed at flexion.

In order to avoid over constraining the knee joint, the load distribution device 100 may include a multi-DOF mechanism 140 which allows multi-directional displacement of the distal 120 support element with respect to the proximal 110 support element.

The load distribution device 100 is basically worn by a user in a fashion similar to conventional limb orthosis and is positioned at the middle of the joint-segments structure of the user's body in order to align the pivot of the compensating joint 130 with the rotational axis of the joint. The user secures the load distribution device 100 using the proximal segment contact elements 114a, 114b, 115a, 115b and distal segment contact elements 124a, 124b, 125a, 125b onto the respective body segments. Depending of the application, the load distribution device 100 can be worn on one or more joint-segments structures of the user's body.

Load Distributor Assembly

The load distributor assembly, which is composed of two on-body dermoskeleton supports referred to as the proximal 110 and distal 120 support elements, is basically designed as a peripheral limb orthosis aiming at stabilizing the joint during extreme activities or for post-surgery procedures.

The proximal 110 and distal 120 support elements are independently connected to the compensating joint 130 for the distribution of additional biomechanical energy, supplied by the compensating joint 130, onto associated body segments of a user.

This overall architecture provides additional biomechanical energy at the joint-segments structure allowing the reduction of the musculo-skeletal stress at the joint of a respective joint-segments structure and consequently, the reduction of the apparent total weight of the user during mobility. Therefore, the load distribution assembly provides active stability with the injection of additional biomechanical energy through a given joint-segments structure as well as passive stability at the respective joint for a full biomechanical support of the structure during normal and highly demanding activities.

The proximal support element 110 is adapted to be positioned onto the proximal body segment of the joint-segments structure of the user and is connected to the stator element of the compensating joint 130. The distal support element 120 is adapted to be positioned onto the distal body segment of the joint-segments structure of the user and is connected to the rotor element of the compensating joint 130. Each of the proximal 112 and distal 122 frame elements includes two pairs of agonist-antagonist contact elements composed of two contact elements 114a, 114b, 115a, 115b, and 124a, 124b, 125a, 125b, respectively, for the transfer of the biomechanical energy from the compensating joint 130 to the associated body segments.

The contact elements 114a, 114b, 115a, 115b, and 124a, 124b, 125a, 125b are specifically designed to mechanically distribute the biomechanical energy supplied by the compensating joint 130 through the proximal and the distal body segments of the joint-segments structure of the user. Therefore, the additional energy generated or dissipated by the joint mechanism 130 during extension/flexion movements of the load distribution device 100 is transferred to the proximal and distal body segments via the contact elements 114a, 114b, 124a, 124b and 115a, 115b, 125a, 125b precisely positioned in an agonist-antagonist configuration in order to optimize the transfer of energy and secure a continuous and direct connection with the body segments of the user.

While the main function of the load distributor assembly is to transfer the additional biomechanical energy supplied by the compensating joint 130 onto the body segments of the user, the proximal 110 and distal 120 support elements and their respective contact elements 114a, 114b, 115a, 115b, and 124a, 124b, 125a, 125b are specifically designed not to interfere with the natural kinetics and kinematics of their associated joint-segments structure, prevent the reduction of performance in the long-term due to displacement or misalignment of the load distribution device 100, and operate the load distribution device 100 without any interaction with the external environment, i.e. the ground.

When the load distribution device 100 is fitted onto a joint-segments structure, the contact elements 114a, 114b, 115a, 115b, and 124a, 124b, 125a, 125b are secured to their respective proximal and distal body segments allowing the alignment of the compensating joint 130 axis with its associated joint axis.

The load distribution device 100 may be, for example, integrated into clothing, for example a pair of pants for the knee-thigh/shank structure embodiment, equipped with a specialized clothing adapter, specifically designed to attach the load distributor assembly onto its associated body segments. In the illustrative embodiment, the load distribution device 100 is firmly attached to both body segments of the user with a set of rigid contact elements 114a, 114b, 124a, 124b and pliant contact elements 115a, 115b, 125a, 125b in the form of restraining straps. This sample configuration improves the efficiency with which the load distribution device 100 is secured onto the joint-segments structure of the user by reducing transversal and coronal displacements that could result in the reduction of the performance of the load distribution device 100. An advantage of this configuration is the coronal stability of the load distribution device 100 on the user's limb. The specialized clothing is adequately secured at each extremities of the joint-segments body structure. For the knee-thigh/shank structure embodiment, the specialized pants are adequately secured at the hip belt and at the level of the ankle. This arrangement ensures that the load distribution device 100 acts as an efficient supportive system firmly stabilized at the coronal plan and prevents the displacement of the load distribution device 100 that consequently would affect its performance because of its non-optimal alignment of with regard to the joint's axis.

Knee-Thigh/Shank Structure Embodiment

The knee-thigh/shank embodiment is intended to assist the user during its locomotion activities. Accordingly, the main goal is to reduce the user's knee torque during its locomotion activities, and particularly when the user has extra payload to carry. It is then necessary to transfer a considerable amount of torque to the shank and thigh in order to significantly reduce the amount of torque the user's knee has to provide. The direction and the magnitude of the applied torque will vary depending on the user's position and activity.

Moreover, the purpose of the load distribution device 100 is to transfer the musculo-skeletal stress applied to the user's knee to the respective leg segments. It is deemed inappropriate to apply any reaction forces to the knee such as additional compressive or shearing forces to the leg segments. Accordingly, the load distribution device 100 applies pure torque on the knee axis, with minimal reaction forces at the leg segments. In order to transfer the motor torque to the leg segments without reaction forces, the load distribution device 100 applies two equal, opposite in direction, forces on both leg segments via the agonist-antagonist configuration of the contact elements 114a, 114b, 124a, 124b, and 115a, 115b, 125a, 125b. The magnitude of the forces to be applied on the segments is determined in accordance with the desired torque and the distance that separates the two opposite forces. In order to reduce the magnitude of the forces applied on the user's leg, the distance between these two forces must be maximal, as expressed by the following equation:

$$F = \frac{T}{d} \qquad \text{EQUATION 1}$$

It has been assessed that to support 40 Kg during flexion, a maximum torque of 50 N*m is necessary. Since the maximal desired torque is 50 N*m and the distance between the contact elements 114a, 114b and 124a, 124b is about 160 mm (typical; determined experimentally), the necessary contact force is then 310 N. It has been assessed experimentally that this force can be supported by the leg tissues in a relatively comfortable manner with 40 mm wide contact elements 114a, 114b and 124a, 124b.

The forces are preferably applied to the leg by compression of the leg tissues. To minimize the movement of the load distribution device 100 on the user's leg, it is desirable to apply these forces with a rigid support. In the illustrative embodiment, the load distribution device 100 then has four rigid contact elements 114a, 114b and 124a, 124b with which to apply the desired pressures to the leg, and four restraining straps to maintain the load distribution device 100 in proper position.

During normal operation, the load distribution device 100 generates torque at the knee in both directions. Since the contact elements 114a, 114b and 124a, 124b can only push on the leg tissues to generate the required force, the opposite direction forces have to be applied by contact elements 115a, 115b and 125a, 125b in the form of restraining straps (the load distribution device 100 pulls on the restraining straps). It is then desirable to determine a preferential direction of torque application. In the preferential direction, the four contact elements 114a, 114b and 124a, 124b are used to apply the required torque on the leg, while in the non-preferential direction, the four straps (i.e. contact elements 115a, 115b and 125a, 125b) are used. It is to be understood that in an alternative embodiment, contact elements 115a, 115b and 125a, 125b may also be rigid instead of being pliant, i.e. restraining straps.

Figure 3A:
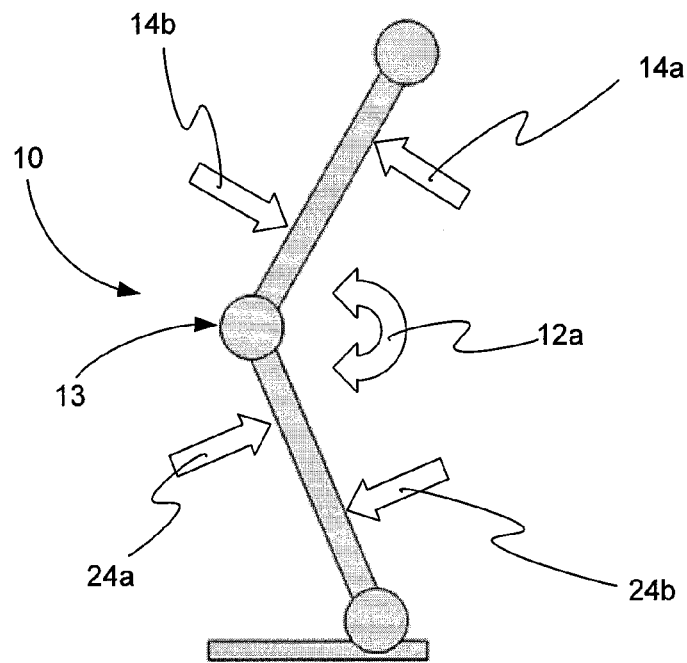
FIGS. 3A and B are schematic representations of the Torque and Forces position definition during extension (FIG. 3A) and flexion (FIG. 3B)

Referring to FIG. 3A, during extension, the knee 13 torque is in the positive direction 12a. This particular activity can be characterized as a positive, varying magnitude torque applied to the knee 13 in the preferential direction. The four force application levers 14a, 14b, and 24a, 24b of the load distribution device 100 are then located in order to provide compressive contact with the leg 10 in the preferential direction, which means a thigh proximal posterior 114a and a thigh distal anterior 114b contact elements corresponding to, respectively, force application levers 14a and 14b, and a shank proximal anterior 124a and a shank distal posterior 124b contact elements corresponding to, respectively, force application levers 24a and 24b. The distance between the levers is maximized in order to minimize the contact pressure on the tissues, while keeping the overall dimensions acceptable.

Figure 3B:
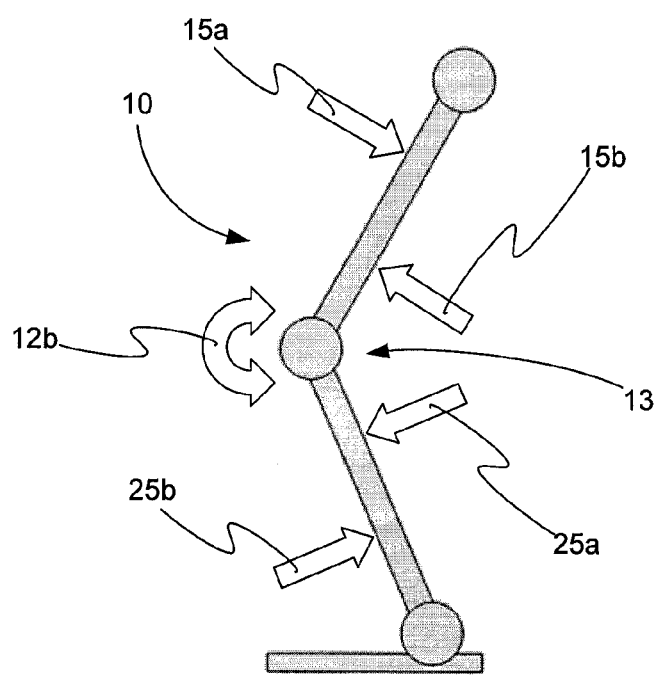

Referring now to FIG. 3B, during flexion, the knee 13 torque is in the negative direction 12b. This particular activity can be characterized as a negative, varying magnitude torque applied to the knee 13 in the non-preferential direction. The four force application levers 15a, 15b, and 25a, 25b of the load distribution device 100 are then located in order to provide compressive contact with the leg 10 in the non-preferential direction, which means a thigh proximal anterior 115a and a thigh distal posterior 115b contact elements corresponding to, respectively, force application levers 15a and 15b, and a shank proximal posterior 125a and a shank distal anterior 125b contact elements corresponding to, respectively, force application levers 25a and 25b. The distance between the levers is maximized in order to minimize the contact pressure on the tissues, while keeping the overall dimensions acceptable.

Control System

Figure 4:
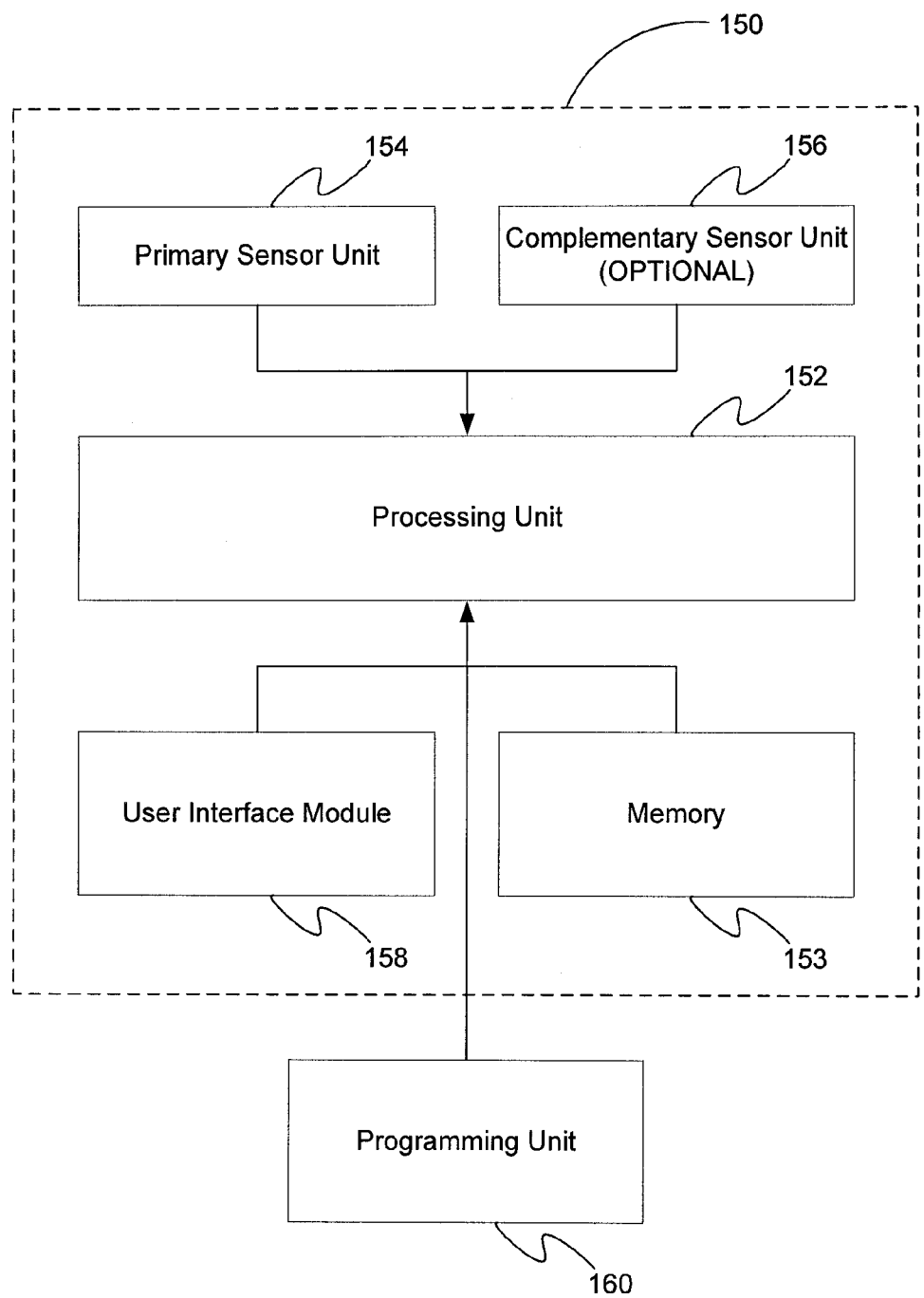
FIG. 4 is a block diagram of the control system for operating the load distribution device of FIG. 1.

Referring to FIG. 4, the control system 150, which may be enclosed in the electronics enclosure 116 (see FIGS. 1 and 2), is operatively connected to the compensating joint 130 and includes a processing unit 152 with an associate memory 153, a primary sensor unit 154, an optional complementary sensor unit 156 and a user interface module 158. A programming unit 160 may further be used to configure the processing unit 152.

The main function of the processing unit 152 is to control the compensating joint 130 to apply forces to the proximal 110 and distal 120 support elements of the load distribution device 100. Coordinating the mechanical elements of the load distribution device 100, the processing unit 152 initiates the compensatory movements of the load distribution device 100 in order to help a user, for example, to stand up, to sit down, to walk on a leveled or irregular ground, to travel up or down inclined planes, to go up or down stairs, to kneel up or down and assist the user in performing various other movements. The processing unit 152 gets user inputs and provides and/or displays feedback information to the user by means of the user interface module 158. The processing unit 152 receives, for example, configuration information such as the user weight, the additional load and the level of assistance which is to be provided and stores that information in its associated memory 153 for subsequent reference.

In order to perform the motion and the force controls required to assist a given joint-segments structure through the use of the load distribution device 100, the processing unit 152 obtains and processes data from a primary sensor unit 154. The primary sensor unit 154 may include, for example, sensors usually used for systems navigation such as, without limiting the present invention to the following sensors, gyroscopes and accelerometers. Other sensing elements providing information on the biomechanical characteristics of the user mobility to the processing unit 152 may also be used. Among other sensing elements, without limiting the present invention to the following sensors, are sensors capable of measuring moments of forces, position and parts movement at the compensating joint 130.

Based on the acquired information, the processing unit 152 calculates the required set-points dedicated for the compensating joint 130 in order to properly actuate the proximal 110 and distal 120 support elements and thus adequately compensate the user's movements.

The optional complementary sensor unit 156 collects further information about the activities performed by the user. When the optional complementary sensor unit 156 is present, the processing unit 152 may combine this further information with the data received from the primary sensor unit 154 in order to determine if the control system 150 is interacting properly. Without limiting the present invention to the following sensors, the complementary sensor unit 156 may include gyroscopes, accelerometers and/or various other sensors that may be used to detect operational dysfunctions of the primary sensor unit 154.

Advantageously, the sensors of the primary 154 and complementary 156 sensor units performs measurements on the load distribution device 100, not the body of the user.

The user interface module 158 is used to select, among other things, the level of the compensation that the compensating joint 130 and the proximal 110 and distal 120 support elements would perform on the corresponding joint-segments of the user. The level of compensation may be selected to be at a minimum level in order to have the control system 150 provide no assistance to the user in any conditions or can be configured at the maximum level to help the user to stand still or to rest in a sitting position using the load distribution device 100. The user interface module 158 may also receive midway levels of compensation so as to further assist the user in carrying a significant additional load.

The programming unit 160 can be used for the configuration of the control system 150 and consists of a computing device such as a personal computer, laptop computer, personal assistant device or any other such device that runs specialized software to interact with the control system 150 through, for example, wireless communication or cables/connectors. The programming unit 160 includes processing software/code, configuration and set-up data, programming parameters, calibration factors, user information and various other parameters that may be used by the processing unit 152 and its associated memory 153 to control the load distribution device 100. Information about the anthropometric measurements of a given human body joint-segments structure and tables of calibration values are examples of data that are managed by the programming unit 160. The programming unit 160 may also pull data from the control system 150 for the purpose of, for example, validation and the preparation of operating reports.

Figure 5:
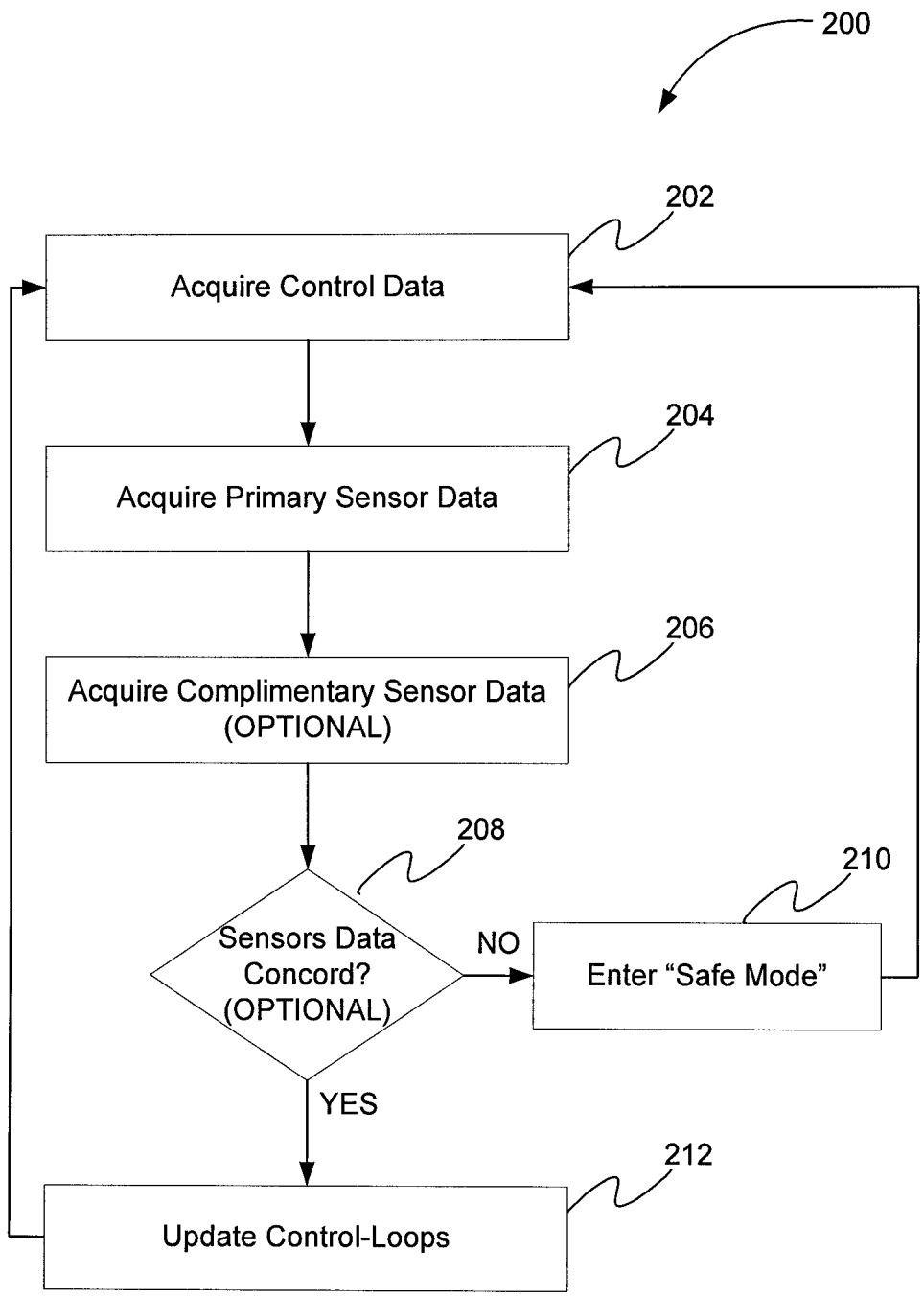
FIG. 5 is a flow diagram of a control process that may be executed by the control system of FIG. 4.

Various algorithms may be implemented on the control system 150 of the load distribution device 100. Referring to FIG. 5, there is shown a flow diagram of an example of a control process 200 that may be executed by the processing unit 152 and stored in its associated memory 153. The steps of the process 200 are indicated by blocks 202 to 212.

The process 200 starts at block 202 by acquiring control data from its associated memory 153 and/or the user interface module 158 and/or the programming unit 160. This control data can include user general information, user anthropomorphic profile, user preferences, real-time user adjustments, etc. This data is used by the processing unit 152 to control the compensating joint 130 and the overall operations of the load distribution device 100.

At block 204, data from the primary sensor unit 154 is acquired. The primary sensor unit provides, for example, measurements of the position of various compensating joint 130 moving parts as well as of moments and forces supplied by the compensating joint 130, and measurements of the acceleration and rotation of the proximal 110 and distal 120 support elements with respect to the ground and the forces developed by the compensating joint 130.

A block 206, if a complementary sensor unit 156 is used, complimentary sensor data is acquired. The complementary sensor unit provides, for example, measurements of the position of various compensating joint 130 moving parts as well as of moments and forces supplied by the compensating joint 130, and measurements of the acceleration and rotation of the proximal 110 and distal 120 support elements with respect to the ground and the forces developed by the compensating joint 130.

Then, at block 208, if the complementary sensor unit 156 is used, the process 200 verifies if the data acquired from the primary sensor unit 154 and the complementary sensor unit 156 concord. If the sensors data do not concord, the process proceeds to block 210 where the load distribution device 100 is forced to enter in a safety mode called "safe mode of operation" as confliction information is being acquired. The process 200 then proceeds back to block 202 where new control data may be acquired or simply go through to block 204 where new primary sensor data is acquired. If the sensors data concord, the process 200 proceeds to block 212.

At block 212, the processing unit 152 process the data supplied by the primary sensor unit 152, and if present the complimentary sensor unit 154, in order to operate a primary control-loop for the control of the compensating joint 130 and a system control-loop to control the overall behavior of the load distribution device 100.

The process 200 then proceeds back to block 202.

Compensating Joint

The compensating joint 130 is an actuating mechanism that exerts angular force (i.e. torque) at the pivot junction of the proximal 110 and distal 120 support elements, in order to allow the load distribution device 100 to perform flexion/extension movements onto a given human body joint-segments structure. Depending on the design of the proximal 110 and distal 120 support elements, the compensating joint 130 generally includes at least one mechatronic motorized system located at the lateral and/or at the medial pivot junction of the proximal 110 and distal 120 support elements.

Various architectures may be envisioned for the compensating joint 130. Without limiting the present invention to the following mechanisms, the compensating joint 130 may be in the form of an electro-mechanical, a hydraulic or a pneumatic mechanism that can generate or dissipate a certain amount of biomechanical energy. Independently of the technical implementation, the main function of the compensating joint 130 is to compensate, in generation and dissipation, a certain amount of biomechanical energy at a human body joint structure in order to maintain, restore or enhance the user's biomechanical capability in mobility.

An example of an electro-mechanical solution that may be used for the compensating joint 130 is the harmonic drive, which may be implemented on one side, i.e. either on the lateral or the medial pivot junction of the load distributing assembly, or on both sides, i.e. both on the lateral and the medial pivot junction of the load distributing assembly. The harmonic drive is a compact transmission mechanism that enables high reduction ratios within a single reduction stage (from 50:1 to 160:1), unlike the more traditional planetary gear units where multiple stages are required to obtain high ratios. Other advantages of this technology are the high torque/weight ratio, the intrinsic zero-backlash design and the possibility to integrate it co-axially with the motor.

The compensating joint 130 based on the harmonic drive design comprises two main components: the transmission and the motor.

Transmission

In the illustrative embodiment, the load distribution device 100 is designed to provide support to the user in the range of about one third of the typical human knee torque. This additional torque capacity is considered sufficient to compensate for the additional effort that would be required when a user carries a load of about 80 Lbs (36 Kg).

It is important that the actuation mechanism, i.e. compensating joint 130, does not interfere with typical human movements such as sitting and kneeling. Consequently, all the components of the compensating joint 130 should be as compact as possible and close to the body of the user.

Weight is also an important parameter to consider, because it may affect the comfort and the efficacy of the load distribution device 100. A heavier device is more demanding for the user and may counterbalance the foreseen advantages of the load distribution device 100.

Considering the above-mentioned factors, an example of a well suited actuation technology is the harmonic drive. The main advantages of this technology are the following:

high torque/volume (and weight) ratio when integrated;
available in component sets (allows for flexible designs);
integrated output bearing available (lower design complexity);
high transmission ratio in a single stage (50:1); and
satisfactory efficiency (about 80%).

In the illustrative embodiment, the harmonic drive used is the SHD series Harmonic Drive supplied by "Harmonic Drive LLC", which incorporates a bearing between the input and the output of the reducer. This integrated bearing allows for a simpler, more accurate and more compact design.

Considering each model's torque and speed capacity, the SHD-20-50 is well suited for present application, namely it has the following characteristics:

momentary peak torque: 69 Nm (requirement is 50 Nm); and
maximum output speed: 130 rpm (120 rpm is required for running at about 10 Km/h).

Based on the documented harmonic drive torque capacity, the expected life of the unit should be well over 1,500 Km of typical walking locomotion.

Motor

A compact and efficient electric-driven technology that can be used for the motor is the brushless DC motor. This type of motor is often sold in separate components (rotor and stator), making it very easy to integrate into a custom design.

The motor needs to provide sufficient torque and speed for the application. The targeted output torque is of 50 Nm, therefore with a transmission ratio of 50:1 the motor needs to be able to provide about 1.2 Nm; after considering mechanical losses of about 20% in the transmission. Furthermore, the motor needs to be able to reach a maximum speed of about 6000 rpm to meet the running speed requirement (120 rpm at the output). A standard frameless motor from Kollmorgen can be used and has the following characteristics:

peak torque=1.53 Nm @ 21.3 A;
torque constant=0.0855 Nm/A;
speed constant=8.95 V/Krpm; and
motor resistance=1.22 Ohms.

Combined with a current amplifier providing 20 A and 48 V, the motor can supply the following to the compensating joint:

output torque of about 57 Nm (50 Nm desired); and
maximum speed of about 107 rpm (120 rpm is required for running at about 10 km/h).

This indicates that the motor/amplifier is the limiting element for the maximum speed.

Integration

Figure 6:
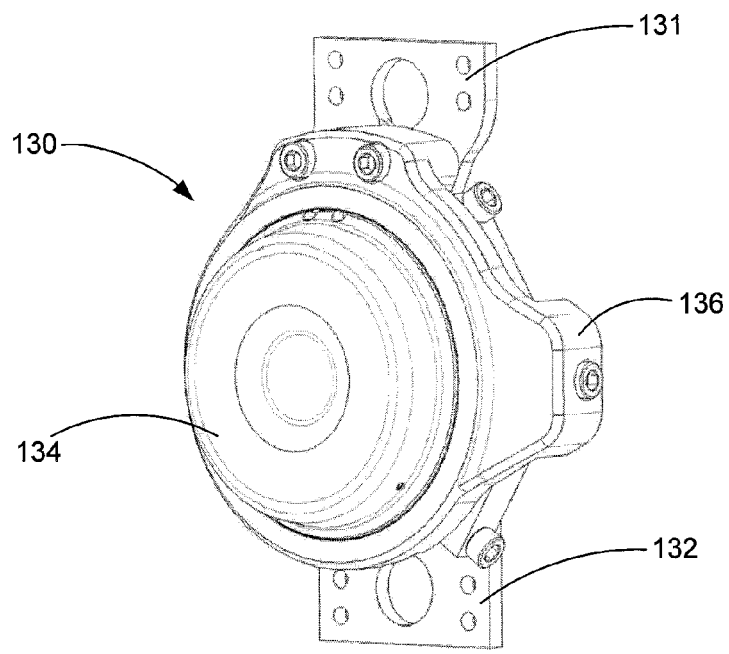
FIG. 6 is a front perspective view of the assembled compensating joint.
Figure 7:
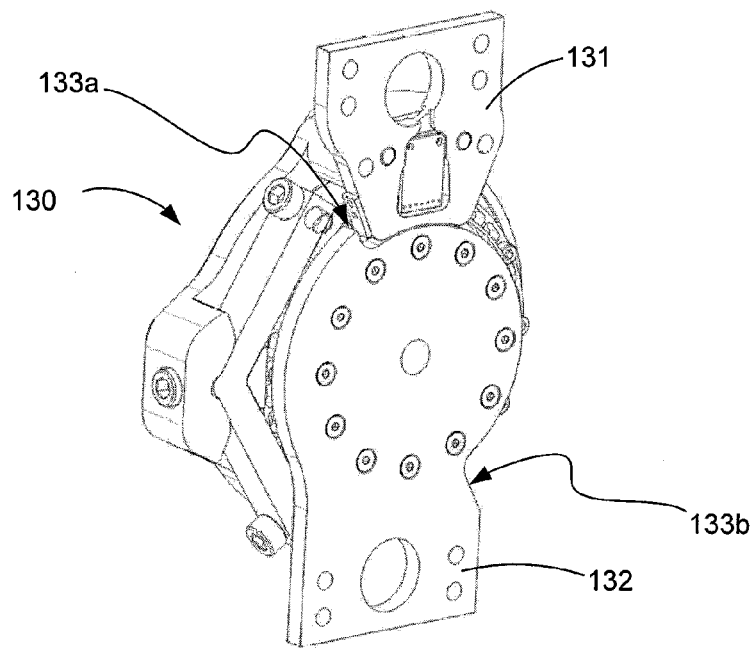
FIG. 7 is a back perspective view of the assembled compensating joint in a first configuration.
Figure 8:
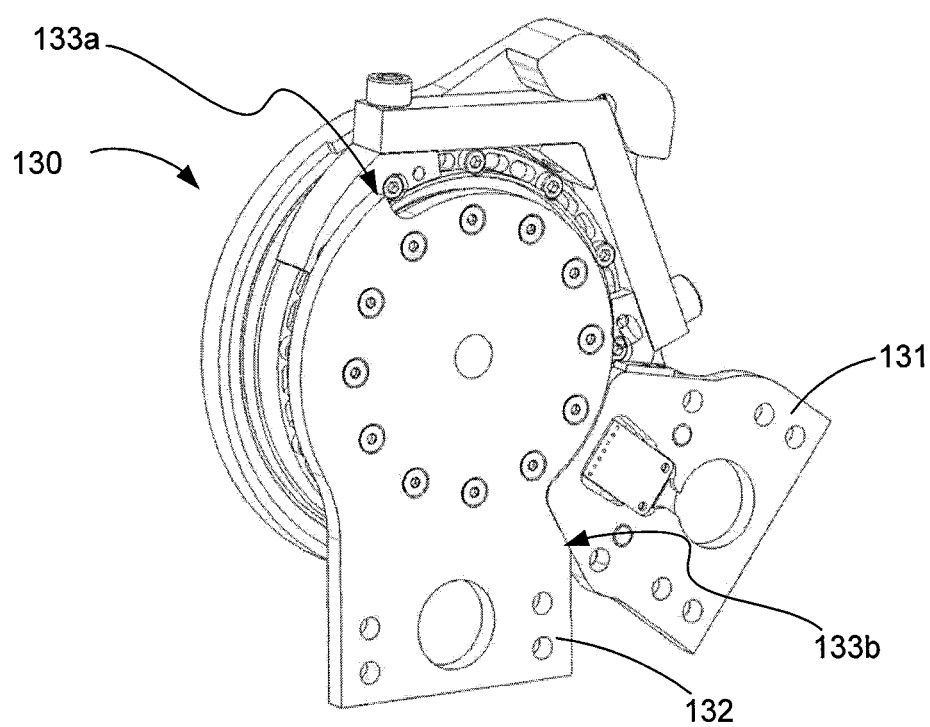
FIG. 8 is a back perspective view of the assembled compensating joint in a second configuration.

Referring to FIG. 6, there is shown a close-up view of the assembled compensating joint 130. The proximal 112 and distal 122 frame elements (see FIGS. 1 and 2) are connected, respectively, to the upper 131 and lower 132 brackets and can rotate relative to one another within about 130 degrees. Referring to FIGS. 7 and 8, the rotation limits are determined by mechanical stops 133*a* and 133*b* that are integrated into the upper 131 and lower brackets 132. The front mechanical stop 133*a* incorporates provision for maximum angle adjustment using spacers of different thickness.

Referring back to FIG. 6, a housing 134 encloses the motor and transmission elements (not shown) of the compensating joint 130.

In the illustrative embodiment, a torque sensor 136 is added at the output of the compensating joint 130 via, for example, a load cell type mechanism attached to the upper bracket 131 but which can rotate relative to the housing 134. The torque sensor 136 is distorted when a torque is exerted by the compensating joint 130 and provides torque data in the form of a signal commensurate with the exerted torque or a torque measurement, depending on the type of sensor used. The torque data can then be used as feedback by the control system 150 (see FIG. 3), providing torque control ability.

Battery Pack

The load distribution device 100 includes a power source in the form of, for example, a battery pack (not shown) for the electrical energy needs of the device's components such as the compensating joint 130 and the control system 150. The battery pack may be composed, for example, of a high-density power module or a network of two or more such modules. The main function of the battery pack is to supply the necessary electrical energy to all electrical-dependant components included in the load distribution device 100 in order to provide for their proper functioning. The location of the battery pack on the human body is application-dependant. Consequently, there is no restriction concerning the positioning of the battery pack. The battery pack can be positioned inside the load distribution device 100, for example inside the electronics enclosure 116, or outside the device for volume optimization purposes.

Various solutions related to high-density power modules are available and many of them meet the functional requirements and the technical specifications of the present invention. To name a few examples, there are custom packageable lithium-ion battery packs from Microsun Inc. and from Energy Dense Power Systems that are suitable for use with the load distribution device 100.

In the illustrative embodiment, the battery pack (not shown) comprises one high-density power module specifically located at the lumbar area of the user's back, attached with a specialized strap-belt accessory that secures the position of the battery pack at the level of the waist. A pair of specialized wires connects the battery pack with each load distribution device 100.

The modular design and the cell-by-cell power management are the main features characterizing a high-density power module.

An example of a high-density power module that may be used with the illustrative embodiment comprises a set of off-the-shelf battery cells where each battery cell may be operated independently, a converter module transferring the power signal between the battery cells and the application load (i.e. the electrical components of each load distribution device 100), a monitoring circuit for the real-time evaluation of the performance and the status of the power modules and its components, and a control system for the management of the charge/discharge process during operation.

The cell-by-cell power management allows the charging and discharging of each battery cell independently of the others, allowing the high-density power module to provide its full power capacity and ensure the balance of the power capacity of each battery cell.

The charging process consists in applying a voltage level on one battery cell of a set showing a power deficiency until voltage/current threshold conditions are met in order to balance the cell to the same power capacity as the others. The discharging process refers to monitoring the power capacity of each battery cell for the detection and measurement of a departing voltage for a given cell. When this occurs, the power capacity of the other battery cells is decreased to reach the same level as the faulty cell. This discharging procedure is then followed by the charging process described above.

By using compact and low-voltage batteries with an application-specific power management, the battery pack allows the building of high-capacity portable/removable power modules within a very restrictive volume and having the capacity to be fully adaptive to complex power-demanding environments.

Although the present invention has been described by way of particular non-limiting illustrative embodiments and examples thereof, it should be noted that it will be apparent to persons skilled in the art that modifications may be applied to the present particular embodiment without departing from the scope of the present invention.

The invention claimed is:

1. A load distribution device for transferring the musculo-skeletal stress at a joint to associated body segments of a given joint-segments body structure of a user, comprising:

a proximal support element adapted to be positioned onto a proximal body segment of the joint-segments body structure, the proximal support element including rigid proximal posterior and distal anterior contact elements configured to exert onto the proximal body segment two opposed pressure areas for the transfer of musculo-skeletal stress from the user's joint to the proximal body segment, and non-rigid proximal anterior and distal posterior elements, the proximal posterior and distal anterior contact elements having spaced apart attachments to the proximal support element;

a distal support element adapted to be positioned onto a distal body segment of the joint-segments body structure, the distal support element including rigid proximal anterior and distal posterior contact elements configured to exert onto the distal body segment two opposed pressure areas for the transfer of the muscolu-skeletal stress from the user's joint to the distal body segment, and non-rigid proximal posterior and distal posterior contact elements, the proximal anterior and distal posterior contact elements having spaced apart attachments to the distal support element;

a torque exerting actuating mechanism movably connecting the proximal and distal support elements;

a control system operatively connected to the torque exerting actuating mechanism; and a power source supplying power to the control system and the torque exerting actuating mechanism;

wherein during user executed movements, the torque exerting actuating mechanism is configured to generate or dissipate, under directions from the control system, a preset level of biomechanical energy corresponding to a user desired musculo-skeletal stress reduction at the joint, the biomechanical energy being transferred from the user's joint onto the proximal and distal body segments via the opposed rigid contact elements.

2. The load distribution device of claim 1, wherein the contact elements are adjustable with three-degrees of freedom including a vertical translation, an antero-posterior translation and a sagittal plane rotation.

3. The load distribution device of claim 1, further comprising a multi-degrees-of-freedom mechanism connecting the torque exerting actuating mechanism to the distal support element, the multi-degrees-of-freedom mechanism being configured so as to allow multi-directional displacement of the distal support element with respect to the proximal support element.

4. The load distribution device of claim 1, wherein the control system includes:

a primary sensor unit providing information on biomechanical characteristics of the movements of the user;

a processing unit; and a memory associated with the processing unit;

wherein the processing unit executes a control process stored in the associated memory, the control process using data from the primary sensor unit to control the torque exerting actuating mechanism.

5. The load distribution device of claim 4, wherein the control process operates a primary control-loop for the control of the torque exerting actuating mechanism and a system control-loop to control the overall behavior of the load distribution device.

6. The load distribution device of claim 4, wherein the control system further includes:

a complementary sensor unit providing information on biomechanical characteristics of the movements of the user;

wherein the processing unit is configured to combine the information provided by the complementary sensor unit with the information provided by the primary sensor unit in order to determine if the control system is interacting properly.

7. The load distribution device of claim 4, wherein the primary sensor unit includes at least one sensor selected from the group consisting of a gyroscope and an accelerometer.

8. The load distribution device of claim 4, wherein the primary sensor unit includes at least one sensor selected from the group consisting of a moments of forces measuring sensor, a position measurement sensor and a parts movement measuring sensor.

9. The load distribution device of claim 4, wherein the control system further includes:

a user interface;

wherein the user interface is used by the user to select a level of compensation to be performed by the torque exerting actuating mechanism.

10. The load distribution device of claim 4, wherein the torque exerting actuating mechanism includes a torque sensor providing data indicative of the torque exerted by the compensating joint and wherein the control process further uses the torque sensor data to control the compensating joint.

11. The load distribution device of claim 1, wherein the torque exerting actuating mechanism includes an actuating mechanism selected from a group consisting of: an electromechanical mechanism, a hydraulic mechanism and a pneumatic mechanism.

12. The load distribution device of claim 1, wherein the torque exerting actuating mechanism includes an electrical motor and the power source is a battery pack.

13. The load distribution device of claim 12, wherein the proximal support element is connected to a stator element of the electrical motor and the distal support element is connected to a rotor element of the electrical motor.

14. The load distribution device of claim 12, wherein the electrical motor includes a harmonic drive.

15. A load distribution system that transfers the musculo-skeletal stress at a joint to associated body segments of a plurality of joint-seginents body structures of a user, comprising a load distribution device according to claim 1 associated with each of the plurality of joint-segments body structures, each load distribution device being adapted for use with its associated joint-segments body structure.

* * * * *